United States Patent [19]

Delmas et al.

[11] Patent Number: 4,501,910

[45] Date of Patent: Feb. 26, 1985

[54] PROCESS FOR TRANSFORMING AN ALDEHYDE INTO AN ALKENE

[75] Inventors: Michel Delmas, Entraygues; Antoine Gaset, Toulouse; Yves le Bigot, Saint Martin de Londres, all of France

[73] Assignee: Agrifurane, S.A., Bon Encountre, France

[21] Appl. No.: 434,048

[22] Filed: Oct. 12, 1982

[51] Int. Cl.$^3$ .......................................... C07D 307/28
[52] U.S. Cl. .................................. 549/506; 549/499; 560/104; 568/652; 568/658; 585/435; 585/638; 585/639
[58] Field of Search ............... 549/499, 506; 560/104; 568/652, 658; 585/435, 638, 639

[56] References Cited

U.S. PATENT DOCUMENTS 4,346,040  8/1982  Delmas et al. ................. 549/506 X Primary Examiner—Richard L. Raymond
Attorney, Agent, or Firm—Harold H. Dutton, Jr.

[57] ABSTRACT

The invention concerns a process transforming an aldehyde into a corresponding alkene, of the type wherein the aldehyde is placed in the presence of a phosphoric reagent and a base in an organic solvent.

The process consists in using an alcohol as the solvent and as a base a mineral base which in an aqueous medium evinces a basic strength equal to or less than that of the hydroxide ion, or a strongly basic organic base of the amine family, and in limiting the hydration rate of the reaction medium to a value at most of 10 moles of water per mole of aldehyde.

10 Claims, No Drawings

PROCESS FOR TRANSFORMING AN ALDEHYDE INTO AN ALKENE

The invention concerns a process for transforming an aldehyde into a corresponding alkene, in particular of the predominant E type. It applies in particular to transforming phenolic aldehydes into corresponding alkenes, also in transforming furfural into diversely substituted furfurylidenes. The term aldehydes as a rule denotes any substance with one or more aldehyde functions.

Presently much use is made of the Wittig reaction, discovered in 1954, for preparing alkenes from corresponding aldehydes; in particular it permits producing alkenes which are or not alpha- or beta-functionalized with a carbon of the double ethylene bond by a cyclic or an aliphatic chain, and non-functionalized from the same carbon by a heteroatom or by a functional heteroatomic group; it is known that this type of alkenes is used in numerous syntheses, or they themselves act in many industrial fields of chemistry (polymers, synthesis intermediates . . . ), in pharmaceuticals (antibacterial agents, analgesics . . . ), in the agro-chemical, foodstuff industries (pheromones, perfumes, insecticides . . . ). The alkenes obtained from the phenol aldehydes or from the derivatives of furfural are particularly active in this latter field, mainly by their antibacterial and antifungal properties.

The Wittig reaction consists of a condensation between a phosphonium salt and a carbonylated compound in the presence of certain strong bases and in a strictly anhydrous aprotic organic medium; the bases used are strong bases of the butyl-lithium type, hydrides . . . which decompose water (the strength of the base exceeds that of the hydroxide ion) and the solvents are organic solvents or slightly basic ones. Producing alkenes by this reaction raises technical problems which are very difficult to overcome on an industrial scale.

In the first place it is difficult to achieve the strictly anhydrous state of the reactive medium in industrial plants, and special and very costly implementing means (drying ovens, drying by nitrogen flow . . . ) are needed. Also, the strong bases that are used react violently and explosively with water, so that storing them is dangerous; again, these products are expensive and considerably increase the cost of synthesizing. Also, the reaction generally is started in heavy solvents (such as dimethylsulfoxide [DMSO], dimethylformamide [DMF], hexamethyl phosphorotriamide [HMPT] . . . ) which are difficult to separate from the reaction products and which cause problems in recycling. Lastly while this reaction offers a satisfactory yield with the aromatic aldehydes, it loses importance with respect to the phenolic aldehydes because the yield becomes low.

In order to eliminate or palliate these defects, much research has been done on the Wittig reaction and two essential types of implementation have been developed. One of these techniques, applied circa 1975 to the Wittig reaction, is that of catalysis by phase transfer (see TETRAHEDRON LETTERS #30, 1974, Pergamon Press UK, W. Takagi et al); this technique allows averting the difficulties relating to the anhydrous state forced on the medium, but it also implies the presence of a substantial and corrosive aqueous phase which thereby restricts its significance; furthermore, the alkene yield is mediocre and the reaction is not stereoselective (the Z/E ratio is about unity). Lastly this technique cannot be applied to the aliphatic and phenolic aldehydes because of secondary reactions taking place; this limitation is a serious drawback in practice because the aliphatic and phenol alkenes are extremely useful substrates, indispensable when synthesizing active products, essential in biochemistry, for instance pheromones, anti-bacterial and prostaglandin products.

Another type of technique, employing a so-called Wittig-Horner reaction derived from the Wittig reaction consists in reacting a phosphonate in the presence of a strong base in a biphase liquid medium consisting of an aqueous phase and an immiscible organic phase. (For more details, see SYNTHESIS, 1976, p. 396, M. Mikolajczyk et al). A variation described in 1979 (SYNTHESIS, 1979, p. 884, Foucault et al) performs the reaction in liquid/solid phases.

However, and as for the previous technique, these techniques are inapplicable to the phenolic and aliphatic aldehydes, which, as already mentioned, represents a serious restriction. Also, they permit producing only alkenes functionalized in alpha or beta of the carbon of the double ethylene bond from the phosphonates, by a heteroatom or a functional heteroatomic group. These alkenes much differ with respect to their activity from the alkenes which are not alpha or beta functionalized, and this limitation further reduces the interest of these methods.

The patent application No. 80.16767 filed by this applicant on July 28, 1980 now U.S. Pat. No. 4,346,040 describes a new process for transforming aldehydes, which eliminates the above mentioned drawbacks of the conventional methods. This process is essentially characterized in that the transformation reaction takes place in an organic, aprotic medium at a low rate of controlled hydration. The process results in a large stereoselectivity for the type Z isomers.

It is the object of the present invention to provide a process originating from an inventive master-concept close to that of the above process and making it possible to eliminate under the same conditions the defects of the classical methods and to obtain predominant type E alkenes. It is known that this type of isomer, contrary to the case for the Z isomer, is active biologically, so that for many applications, its production in predominant form will be of capital significance.

In particular it is the object of the invention to provide a process for producing alkenes which are or not alpha- or betafunctionalized in the carbon of the double ethylene bond, from a phosphoric reagent, by a cycle or an aliphatic chain or a heteroatomic functional group.

Another object of the invention is to disclose a process which can be satisfactorily implemented both with aromatic and heteroatomic phenolic aldehydes and aliphatic aldehydes to achieve the type of alkenes mentioned above.

Another object is to eliminate the strict need for the anhydrousness of the Wittig reaction by providing a process which can be carried out under high-performance conditions in the presence of water.

Another object of the invention is to disclose a process which is operative with a light solvent, of low cost, amenable to regeneration and the synthesis products of which are easily separated.

Another object is to disclose a process releasing a nonexothermal reaction, without any danger even when large amounts of products are mutually present, and taking place under gentle conditions of temperature and pressure.

Another object is to disclose a process making it possible to precisely set the stereoselectivity of the reaction in order to simultaneously obtain an alkene of the predominant E type and an alkene of the Z type in the desired proportions.

To that end, the transformation process object of the invention is of that type wherein the aldehyde is placed in the presence of a phosphoric reagent and a base in an organic solvent; according to the present invention, to produce a predominant E type alkene, the reaction is carried out in the following conditions:

an alcohol is used as the solvent;
a mineral base is used, which in an aqueous medium has a basic strength less than or equal to that of the hydroxide ion, or a strong organic base of the amine family;
and the hydration rate of the reactive medium is restricted to a value at most 10 moles of water per mole of aldehyde.

Experiment has surprisingly shown that using an alcohol as the solvent (an essential condition) in conjunction with controlling the hydration rate and using a base from the cited group allow selectively transforming the aldehyde into an alkene of the predominant E type at high yields. Using the solvent in the above cited conditions entails no practical difficulty whatever, in the light of this harmless substance being commonplace and highly economical. The hydration rate can be easily controlled within the limits specified and therefore the difficult Wittig-reaction conditions are thus eliminated.

The alcohols which appear to offer the best yields are methanol and ethanol, which therefore shall be used preferentially; be it noted that these alcohols are subsequently easily separated from the reaction medium and easily recycled.

In a preferred mode of implementation, the amount of alcohol is advantageously adjusted in a manner to achieve an aldehyde dilution between about 0.2 and 2 moles of aldehyde per liter of alcohol.

Moreover the base being used can be a conventional base, in particular an ion compound of alkali metals wherein the anion evinces a basic nature, in particular an ion compound of potassium, of rubidium or of cesium; this type of base entails no risks whatever on the industrial scale and its cost is modest.

Furthermore it has been found that this reaction also is operative at good yields with the phenolic, aromatic, heteroatomic, aliphatic aldehydes, whether functionalized or not. The process conditions permit inhibiting secondary aldolization reactions, which explains the yields obtained from aliphatic aldehydes also being of high values.

It should be borne in mind that in the case of the aromatic aldehydes, a secondary reaction (termed the Cannizaro reaction) sometimes takes place in the conventional methods, which limits the alkene yield. As regards the process of the invention, this reaction is hardly sensible at all; it will be totally inhibited when the base used is the carbonate of potassium, or rubidium or cesium.

The reaction of the process of the invention is slightly endothermic and causes no danger at all of abrupt steps. The yield is improved by slightly heating; practically, the reaction medium can be kept at ambient temperature, the operative reaction being within the range from $-30°$ C. to $+120°$ C.

Also, regarding the relative product quantities, the following conditions are advantageous for operation:

the base is used in a slightly excessive amount over stoichiometry with respect to the aldehyde,
the phosphoric reagent is used in slightly stoichiometric excess with respect to the aldehyde.

The phosphoric reagent used can be a phosphonium, phosphonate or phosphorous salt and makes it possible to produce an alkene, whether functionalized or not in alpha or beta of the double ethylene bond from the carbon of the latter and obtained from the phosphorous salt. These alkenes are significant in practice, applying widely and diversely to agro-chemistry, to pharmaceuticals and the chemical industry, both on account of their biological activities proper and as synthesis intermediates; the invention thus offers the substantial advantage of making it possible to point the reaction in the direction of this type of compound production.

Furthermore the process of the invention where desired permits adjusting the reaction stereo-chemistry, the type E alkenes obtained being of the predominant kind. To that end, the process adds to the main solvent, consisting of the alcohol, an aprotic solvent, in particular dioxane or dimethoxyethane (DME), or methylene chloride or nitrobenzene. The stereochemistry of the reaction is determined by the proportion of the two solvents, and the reaction thusly can be adapted to the contemplated application.

The invention outlined is illustrated in non-restrictive manner below by examples of implementation.

EXAMPLE 1

Hydroxy-1, methoxy-2, (pentene-1)yl-4 benzene is synthesized from vanillin in the presence of potassium carbonate and butyl-triphenyl-phosphonium bromide in methanol.

0.12 moles of phosphonium salt, 0.12 moles of potassium carbonate, 0.1 moles of aldehyde in 100 ml of commercial methanol are placed in a 1-liter reactor.

After reacting for 1 h at ambient temperature, the reaction medium is filtered and concentrated. The alkene formed is obtained after distillation (b.p.: $90°$ C./0.5 mm Hg) at a yield close to 85% and is characterized by its infrared and NMR spectra.

The reaction is stereo-selective and the E isomer is predominant (% of E isomer/% of Z isomer=85/15). No other known process offers this result.

The phenol aldehydes which thus can be made valuable for the most part are extracted from vegetal matter, in particular by biologically or chemically treating lignin.

EXAMPLE 2

Hydroxy-1, methoxy-2, (heptene-1)yl-4 benzene is synthesized from vanillin in the presence of potassium flouride and hexyl-triphenylphosphonium bromide in methanol.

0.12 moles of phosphonium salt, 0.12 moles of potassium fluoride, 0.1 moles of aldehyde in 100 ml of commercial methanol are placed in an identical 1-liter reactor.

Following $2\frac{1}{4}$ h of agitation at ambient temperature, the hydroxy-1, methoxy-2, (heptene-1)yl-4 benzene is obtained in pure form, with a yield of 88%, by distilling in vacuum (b.p. $115°$ C./0.8 mm Hg).

The reaction's stereoselectivity results in a product mostly E (% isomer E/% isomer Z=87/13).

The antibacterial activity of this product is shown by its phenol coefficient at $37°$ C.:

625 for St. Aureus 667 for M. Tuberculosis
556 for C. Albicans.

EXAMPLE 3

Isoeugenol is synthesized from vanillin in the presence of potassium carbonate and ethyl triphenyl phosphonium bromide in commercial methanol.

0.025 moles of potassium carbonate, 0.025 moles of phosphonium salt, 0.02 moles of aldehyde and 20 ml of commercial methanol are placed into a 250 ml reactor.

The medium is agitated for one of the conditions below in each case:
5 h at −10° C.
2½ h at 0° C.
1 h at 20° C.
½ h at 40° C.

These conditions permit completely transforming vanillin into eugenol. Following distillation, the isoeugenol is identified by comparing its physicochemical properties with those of the commercial product.

EXAMPLE 4

Hydroxy-1, (butene-1)yl-2 benzene is synthesized from salicylic aldehyde in the presence of cesium carbonate and propyl-triphenyl phosphonium bromide in methanol.

0.025 moles of phosphonium salt, 0.025 moles of cesium carbonate and 0.02 moles of aldehyde in 20 ml of commercial methanol are mixed in a reactor.

The reaction mixture is agitated at ambient temperature for 1½ h. The hydroxy-1, (butene-1)yl-2 benzene (% of E isomer/% of Z isomer=82/18) is obtained by distillation (b.p. 75° C./1 mm Hg) in pure form with a yield of about 80%. It is characterized by its infrared and nuclear-magnetic resonance spectra, and these results are confirmed by microanalysis.

EXAMPLE 5

Hydroxy-1, vinyl-4 benzene is synthesized from hydroxy-4 benzaldehyde in the presence of potassium carbonate and methyltriphenylphosphonium bromide in methanol.

0.025 moles of phosphonium salt, 0.025 moles of potassium carbonate and 0.02 moles of hydroxy-4 benzaldehyde in 20 ml of commercial methanol are placed into a 250 ml reactor.

The reaction mixture is agitated at ambient temperature for 4 h. The major part of the triphenylphosphine oxide formed is precipitated and separated by filtering the organic phase which is then chromatographically analyzed in the vapor phase in a column of the OV 101 type. The hydroxy-1 vinyl-4 benzene so obtained is produced with a yield close to 90% after distillation.

EXAMPLE 6

(Butene-1)yl-2 furan is synthesized from furan-2-carboxaldehyde in the presence of potassium carbonate and propyltriphenyl phosphonium bromide in ethanol.

0.025 moles of phosphonium salt, 0.025 moles of potassium carbonate and 0.02 moles of aldehyde in 20 ml of ethanol are placed in a reactor of 250 ml at a temperature of 95° C.

The reaction mixture is agitated for 2 h at the ethanol reflux. These conditions permit completely transforming furfural into (butene-1)yl-2-furan which is extracted after filtration and concentration of the reaction medium by chromatography in a short column of silica gel using hexane as the eluant.

The reaction is stereoselective and the E isomer so obtained is predominant (% of E isomer/% of Z isomer=70/30).

The initial compound furan 2-carboxaldehyde (or furfural) is produced industrially from agricultural byproducts rich in pentosanes (corn stalks, rice and oat chaff, sugar-cane trash, peanut shells and wood wastes). These wastes are treated in a medium of concentrated acid to produce also pentoses by hydrolyzing their pentosanes which dehydrate to result in furfural.

EXAMPLE 7

(Pentene-1)yl-2 furan is synthesized from furan-2-carboxaldehyde in the presence of potassium carbonate and butyltriphenylphosphonium bromide in methanol.

0.025 moles of phosphonium salt, 0.025 moles of potassium carbonate and 0.02 moles of furfural in 20 ml of commercial methanol are placed in an identical 250 ml reactor.

The reaction mixture is raised to reflux and kept agitated for 1¼ h. The (pentene-1)yl-2 furan (% of E isomer/% of Z isomer=69/13) is obtained in pure form with a yield of about 85% after filtration and rapid chromatography on silica gel.

EXAMPLE 8

(Pentene-1)yl benzene is synthesized from benzaldehyde in the presence of potassium carbonate and butyl-triphenyl phosphonium bromide in a mixture of dioxane-1,4 and methanol.

0.025 moles of phosphonium salt, 0.025 moles of potassium carbonate and 0.02 moles of benzaldehyde in 20 ml of a mixture of dioxane-1,4 and commercial methanol are placed in a reactor.

Following 2½ h of boiling, the reaction medium is filtered to eliminate the major part of triphenylphosphine oxide formed. Following evaporation of the solvent, the (pentene-1)yl benzene is chromatographed in a short silica-gel column; the eluent is hexane; no matter what the percentage of methanol in the solvent mixture, the olefin yield is close to 95%.

The reaction stereoselectivity depends on the quantity of methanol in the medium:
for 1 ml of methanol, there is 30% of E isomer
for 3.5 ml of methanol, there is 50% of E isomer
for 5 ml of methanol, there is 64% of E isomer
for 20 ml of methanol, there is 77% of E isomer.

EXAMPLE 9

Anethole is synthesized from anisaldehyde in the presence of rubidium carbonate and ethyl-triphenyl phosphonium bromide in methanol.

0.02 moles of anisaldehyde and 20 ml of commercial methanol are added to 0.025 moles of phosphonium salt and 0.025 moles of rubidium carbonate.

The reaction medium is agitated by refluxing the methanol for 3 h. The anethole (% of E isomer/% of Z isomer=67/33) is obtained in pure form with a yield close to 85% and is identified by comparison with the commercial product and by analysis of its NMR and infrared spectra.

The trans-anethole, which is the predominant product of this synthesis, evinces a marked insecticidal character and is a very important substance in the foodstuff field.

EXAMPLE 10

Tetradecene-5 is synthesized from decanal in the presence of potassium carbonate and butyl-triphenylphosphonium bromide in butanol-1.

0.025 moles of phosphonium salt, 0.025 moles of potassium carbonate, 0.02 moles of aldehyde and 0.04 moles of water are mixed in 20 ml of butanol-1 in a reactor.

The reaction medium is made to reflux and kept agitated for 3½ h. The corresponding alkene is obtained by chromatography in a column with a yield of 70% and is characterized by its nuclear-magnetic resonance and infrared spectra and by microanalysis.

The reaction is stereoselective and the E isomer is obtained predominantly (% of E isomer/% of Z isomer=70/30).

These isomers can be separated chromatographically with a column of alumina impregnated with 20% of silver nitrate.

It should be noted that under these empirical conditions, the secondary aldolization reaction will be inhibited.

EXAMPLE 11

Ethyl phenyl-3 propenoate is synthesized from benzaldehyde in the presence of potassium carbonate and of ethyl dimethylphosphono-acetate in ethanol.

0.025 moles of phosphonate, 0.025 moles of potassium carbonate and 0.02 moles of aldehyde are mixed in 20 ml of commercial ethanol in a reactor.

The reaction mixture is agitated at the ethanol reflux for 1 h. These conditions make it possible to completely transform benzaldehyde into ethyl phenyl-3 propenoate which is extracted after filtering and concentrating the reaction medium by silica-gel column chromatography using a mixture of hexane and ether as the eluent.

The reaction is stereoselective and the E isomer is obtained predominantly (% of E isomer/% of Z isomer=86/14).

The reaction yield after the purification is about 88%. The ethyl phenyl-3 propenoate is characterized by its nuclear magnetic resonance and infrared spectra, of which the results are confirmed by microanalysis.

EXAMPLE 12

Ethyl furyl-3 propenoate is synthesized from furfural in the presence of potassium carbonate and ethyl dimethylphosphonoacetate in ethanol.

0.025 moles of phosphonium salt, 0.025 moles of potassium carbonate, 0.02 moles of aldehyde in 20 ml of ethanol at 95% are placed in a 250 ml reactor.

The reaction mixture is raised to reflux and kept agitated for 1 h. The ethyl furyl-3 propenoate (% of E isomer/% of Z isomer=90/10) is obtained in pure form with a yield close to 80% after filtration and chromatography on silica gel.

It must be borne in mind that the stereo-chemistry of the alkene obtained from phosphonates is independent of the solvent; whether the reaction be carried out in dioxane, in ethanol or in a mixture of these two solvents, the preferential E stereochemistry is invariant.

We claim:

1. A process for transforming an aldehyde into a corresponding alkene of the predominantly E type comprising placing an aldehyde in an alcohol solvent in the presence of a phosphoric reagent and a base, said base being selected from the group consisting of mineral bases evincing a basic strength less than or equal to the basic strength of the hydroxide ion, and organic amine bases, and limiting the hydration rate of the reaction medium to a value of approximately 10 moles of water per mole of aldehyde.

2. A process as in claim 2 and wherein said solvent is selected from the group consisting of methanol and ethanol.

3. A process as in claim 1 and wherein said base comprises a salt of an alkali metal selected from the group consisting of potassium, rubidium and cesium.

4. A process as in claim 1 and including carrying out the reaction at ambient temperature.

5. A process as in claim 1 and including adjusting the quantity of alcohol so as to achieve an aldehyde dilution of approximately 0.2 to 2 moles of aldehyde per liter of alcohol.

6. A process as in claim 1 and wherein said phosphoric reagent is selected from the group consisting of phosphonium salts and phosphonate salts.

7. A process as in claim 1 and wherein said phosphoric reagent is present in a slight stoichiometric excess with respect to said aldehyde.

8. A process as in claim 1 and including adding to said solvent an aprotic solvent selected from the group consisting of dioxane, dimethoxyethane, methylene chloride and nitrobenzene.

9. A process as in claim 1 and wherein said aldehyde is a phenol aldehyde extracted from lignin and said base is a mineral base other than soda and potash.

10. A process as in claim 1 and wherein said aldehyde is furfural and said alkene is furfurylidene.

* * * * *